United States Patent
Khaledian et al.

(10) Patent No.: US 12,292,306 B2
(45) Date of Patent: May 6, 2025

(54) OPTIMIZED SOIL SAMPLING FOR DIGITAL SOIL FERTILITY MAPPING USING MACHINE LEARNING AND REMOTELY-SENSED INFORMATION

(71) Applicant: SOILSERDEM LLC, Ames, IA (US)

(72) Inventors: Yones Khaledian, Ames, IA (US); Daniel Linton, Ames, IA (US)

(73) Assignee: SOILSERDEM LLC, Amen, IA (US)

( * ) Notice: Subject to any disclaimer, the term of this patent is extended or adjusted under 35 U.S.C. 154(b) by 300 days.

(21) Appl. No.: 17/877,909

(22) Filed: Jul. 30, 2022

(65) Prior Publication Data

US 2023/0032688 A1 Feb. 2, 2023

Related U.S. Application Data

(60) Provisional application No. 63/227,563, filed on Jul. 30, 2021.

(51) Int. Cl.
| | |
|---|---|
| G01C 21/00 | (2006.01) |
| G01N 33/24 | (2006.01) |
| G01S 17/89 | (2020.01) |
| G06N 3/08 | (2023.01) |

(52) U.S. Cl.
CPC ..... *G01C 21/3826* (2020.08); *G01C 21/3852* (2020.08); *G01N 33/24* (2013.01); *G01S 17/89* (2013.01); *G06N 3/08* (2013.01); *G01N 33/245* (2024.05)

(58) Field of Classification Search
CPC ............ G01C 21/3826; G01C 21/3852; G01N 33/24; G01N 33/245; G01S 17/89; G06N 3/08

See application file for complete search history.

(56) References Cited

U.S. PATENT DOCUMENTS 11,704,581 B1 * 7/2023 McEntire ................. G06N 5/04
706/11
2020/0256978 A1 * 8/2020 Klein ................... G01S 13/9005

OTHER PUBLICATIONS

U.S. Appl. No. 11/704,581-B1 with Paragraph Numbering for Easier Reference (Year: 2023).*
Minasny, B. and Mcbratney, A.B., Digital Soil Mapping: a Brief History and Some Lessons, Geoderma 264, 2016, pp. 301-311.

* cited by examiner

Primary Examiner — Andrew J Cromer
(74) Attorney, Agent, or Firm — LAZARIS IP

(57) ABSTRACT

A soil modeling and mapping framework for use in precision agriculture analyzes remotely-sensed data pertaining to characteristics of one or more agricultural fields, and determines optimal sampling locations from information in remotely-sensed information, terrain derivatives and satellite imagery, to develop a customized sampling design for modeling soil properties in such agricultural fields that optimized for the particular landscape in such fields. The soil modeling and mapping framework then analyzes soil samples collected based on the customized sampling design in machine learning-based models that predict soil properties in sampled, semi-sampled, and unsampled target fields. The predicted soil properties are used to develop highly-accurate maps of soil properties such as fertility maps, which may further be used for defining and creating one or more management zones with recommendations for applying the right amount of nutrients at variable rates in the correct areas.

20 Claims, 5 Drawing Sheets

OPTIMIZED SOIL SAMPLING FOR DIGITAL SOIL FERTILITY MAPPING USING MACHINE LEARNING AND REMOTELY-SENSED INFORMATION

CROSS-REFERENCE TO RELATED PATENT APPLICATION(S)

This patent application claims priority to U.S. provisional application 63/227,563, filed on Jul. 30, 2021, the contents of which are incorporated in their entirety herein. In accordance with 37 C.F.R. § 1.76, a claim of priority is included in an Application Data Sheet filed concurrently herewith.

FIELD OF THE INVENTION

The present invention relates to soil sampling, modeling, and mapping within the field of precision agriculture. Specifically, the present invention relates to systems and methods for developing highly accurate soil maps using machine learning-based soil sampling design strategies and spatial modeling of targeted geographical locations, to predict soil properties such as fertility.

BACKGROUND OF THE INVENTION

Economic and environmental issues related to farming have created at least two major challenges for the agriculture industry over the last several decades. The high demand for producing more food is placing tremendous pressure on agricultural productivity; and, environmental and social challenges have placed increasing pressure on farmers and growers to adopt and implement conservation practices. To deal with these competing issues, agronomists develop management zones (e.g., fertilizer or nutrient recommendation zones) to concurrently maximize production and minimize environmental impacts. However, existing techniques for developing management zones are not efficient for multiple reasons. Perhaps the primary reason is that existing management zones are created from low-quality maps of soil fertility. For example, many growers apply inaccurate amounts of fertilizers (by either over-applying or under-applying) due to poor-quality management zones. Another reason is simply that some entities supply detailed (i.e., high spatial resolution), but not necessarily accurate, management zones that include lots of information, but such information is not understandable to farmers for practical use. For this reason, farmers will be more dependent on agriculture cooperatives to implement the complex delineations of these management zones using sophisticated fertilizer spreaders, and will delegate such activities hoping for best-case outcomes.

Conventional soil mapping methods are inefficient for multiple reasons. The first reason is lack of appropriate data collection methods and analysis. For example, existing methods for making soil fertility maps are based on inefficient sampling designs and lack accuracy. A regular grid of samples—a common industry practice—may cover the geographic space of a field; however, it may not capture the full range of soil property variation within the feature space, leading to bias. For example, if a specific soil type is dominant inside a field, the majority of grid samples will be taken within it. Thus, the grid samples might underrepresent the actual variations inside the field. A grid-sampling design is analogous to a game of "Battleship," wherein a systematic approach is used to compensate for blindly searching for differences in soil properties.

Many conventional soil mapping methods do not involve environmental features to capture the soil variations of the landscape. At most, the agricultural industry usually uses remote sensing data [e.g., the normalized difference vegetation index (NDVI)], to identify management zones and predict crop yield, but it has not been used to predict soil properties.

Conventional methods for producing the maps do not leverage the utility of remotely sensed data and fail to fully represent variation in the field. If agronomists use any spatial modeling methods, they usually create soil fertility maps based on spatial autocorrelation, which carry unique weaknesses. Precision agriculture divisions from agricultural cooperatives and independent agronomists alike have sought to improve the spatial resolution of the soil-fertility maps by using kriging, however, the accuracy of the map they resolve is not improved. While the outward appearance of maps may improve, they are often not using the method correctly; the resource costs using kriging are high, especially for small fields, as the method requires a minimum number of samples (at minimum 100) to support its prediction method. Specifically, spatial autocorrelation models such as kriging rely on the assumption that the target soil property maintains the same normal distribution throughout the map area. In addition, spatial autocorrelation models are incapable of being extended to areas beyond the field sampled.

Thus, there is a critical need in the existing art to improve soil sampling design. There is also a critical need in the existing art to improve the quality of soil fertility and nutrient maps without increasing input expenses for agronomists and farmers. There is a further critical need in the existing art for flexible techniques that produce either simple (coarse spatial resolution) or precise (fine spatial resolution) management zones, depending on the specific needs of each particular user, from high-resolution soil fertility maps.

SUMMARY OF THE INVENTION

The invention described herein can be used for a variety of agronomic information scenarios where soil properties define the base level of information. The technologies describe a soil modeling and mapping framework which create maps which support agronomic activities such as nutrient management, planting population planning, irrigation planning, etc. Where previous soil surveys and zone map models functioned on classifying landscapes with lack of efficiency and practicality, the present invention relates the factors of soil formation to more properly represent soil data on a sub-field-basis to support soil fertility mapping.

The present invention provides a software-based framework that utilizes optimized soil sampling combined with multiple applications of machine learning to model and predict soil properties, e.g., macronutrients, micronutrients, and soil health properties, in both sampled and unsampled fields, and a mapping tool that takes those properties and provides farmers and other users with high-quality maps of such properties. Improvements in the quality of fertility maps based on such modeling of soil properties allow agronomists and farmers to target locations for distribution of nutrients such as fertilizers where they are most needed, and at the times they are most needed, to maximize yield potential, decrease water usage, and minimize risks from both over-applying and under-applying nutrients. Such improvements can be realized by utilizing soil samples that are collected using novel approaches to analyzing remotely-sensed data, including Light Detection and Ranging (LiDAR) information (terrain derivatives) and satellite imagery, that aid in developing optimal soil sampling designs, and applying specific machine learning tools to information collected from such soil samples, to generate higher quality digital soil fertility maps and more accurately define management zones based on such maps.

The present invention creates such soil fertility maps by, in one aspect of the present invention, selecting optimal soil sampling locations by analyzing remotely-sensed data pertaining to one or more fields, selecting optimal predictive variables representing soil properties from a dataset curated from soil samples and the remotely-sensed data, and applying the dataset and the predictive variables to machine learning models that predict soil properties. These predictions can be made for sampled fields and beyond, to fields in which no soil samples were taken. The predicted soil properties are therefore enhanced by the advanced analytics used to identify optimal locations for soil samples that provide a more comprehensive representation of the field's soils across the entire terrain of a field, and generate a set of predictive variables that more accurately represent conditions within those soils, to produce higher quality soil fertility maps.

The present invention includes several elements that provide a clear competitive advantage for producing soil fertility maps. One such element is the use of LiDAR information to create digital hillslope positions (DHP) to optimize sampling locations, which has never been previously applied to soil sampling in production agriculture. The agricultural industry has previously relied on grid sampling or zone sampling, based on existing soil survey maps, for decades. These common industry practices of sampling may cover the geographic space of a field; however, they may not capture the full range of soil property variation within the feature space, leading to bias. The soil sampling aspect of the software framework and mapping tool of the present invention improves the capture of soil variability within fields.

Another element includes the application of advanced machine learning algorithms in combination with remotely-sensed information, weighted with optimized predictive variables, to predict soil fertility properties. At most, the agricultural industry uses remotely-sensed data such as the normalized difference vegetation index (NDVI) to identify management zones and predict crop yield, and remotely-sensed data has not been previously used to predict soil properties in a manner that farmers could reliably base their management plans upon. The applications of machine learning described herein enable prediction of those soil properties with far fewer samples; as the machine learning-based model of the present invention becomes stronger with improved training models and datasets, fewer and fewer samples will be needed in each field. Current industry practices rely on a relatively high sampling density and can only improve accuracy by increasing the quantity of samples taken. Conversely, machine learning models of the present invention, and using remotely-sensed information, will realize benefits from improvements in the sampling methods described herein.

It is one objective of the present invention to provide systems and methods for determining optimal soil sampling locations in a field from remotely-sensed data. It is another objective of the present invention to provide systems and methods that identify optimal variables predictive of soil properties from such samples and such remotely-sensed data. It is a further objective of the present invention to provide systems and methods for determining optimal soil sampling locations in a field, and identifying optimal variables predictive of soil properties, within a framework that analyzes information from both remotely-sensed data and user-provided inputs using machine learning-based tools that predict soil properties from soil samples in both sampled, semi-sampled, and unsampled fields. It is still a further objective of the present invention to provide systems and methods of applying this framework to develop more accurate soil fertility maps from predicted soil properties, and further to apply such maps to more accurately define management zones for applications of soil fertility treatments and/or managing soil conditions within sampled, semi-sampled and unsampled fields. It is yet another objective of the present invention to provide systems and methods of applying this framework to initiate agricultural activities based on soil fertility maps from predicted soil properties, such as initiating automated soil treatments and other actions.

Other objectives, embodiments, features, and advantages of the present invention will become apparent from the following description of the embodiments, taken together with the accompanying drawings, which illustrate, by way of example, the principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

DETAILED DESCRIPTION OF THE EMBODIMENT(S) OF THE INVENTION

In the following description of the present invention, reference is made to the exemplary embodiments illustrating the principles of the present invention and how it is practiced. Other embodiments will be utilized to practice the present invention and structural and functional changes will be made thereto without departing from the scope of the present invention.

The present invention is a soil modeling and mapping framework 100 for use in precision agriculture, for improving the quality and utility of maps of soil properties such as fertility maps. The present invention analyzes environmental features and land management pertaining to one or more target fields at a geographical location, and determines optimal sampling locations from remotely-sensed data for a collection of soil samples, in a customized sampling design for the one or more fields being analyzed. The present invention analyzes soil samples collected according to such a customized sampling design in one or more machine learning-based models that predict soil properties in the one or more fields. These predicted soil properties are then used to generate more accurate soil maps representing such properties, such as soil fertility. It is to be understood that further modifications to, and embodiments and use cases of, the systems and methods described within the process and framework of the present invention are contemplated and considered, as would normally occur to one skilled in the art and science to which these systems and methods relate.

Examples of novel systems and methods of the present invention are presented and described herein, which illustrate workflows and processes of the soil modeling and mapping framework 100 for providing agronomists, farmers, natural resource managers, and others to make management decisions that benefit operations or biological systems of which they are stewards. These examples serve to further illustrate how the present invention is applied to characterize chemical, physical, and biological properties of target fields' soils, to inform more granular, site-specific management.

It is to be noted that, as used herein, "optimal" or "optimized" mean designed, specified, or customized for the task at hand. These words therefore do not indicate or constitute an absolute "best" for any purpose to which they are applied.

Figure 1:
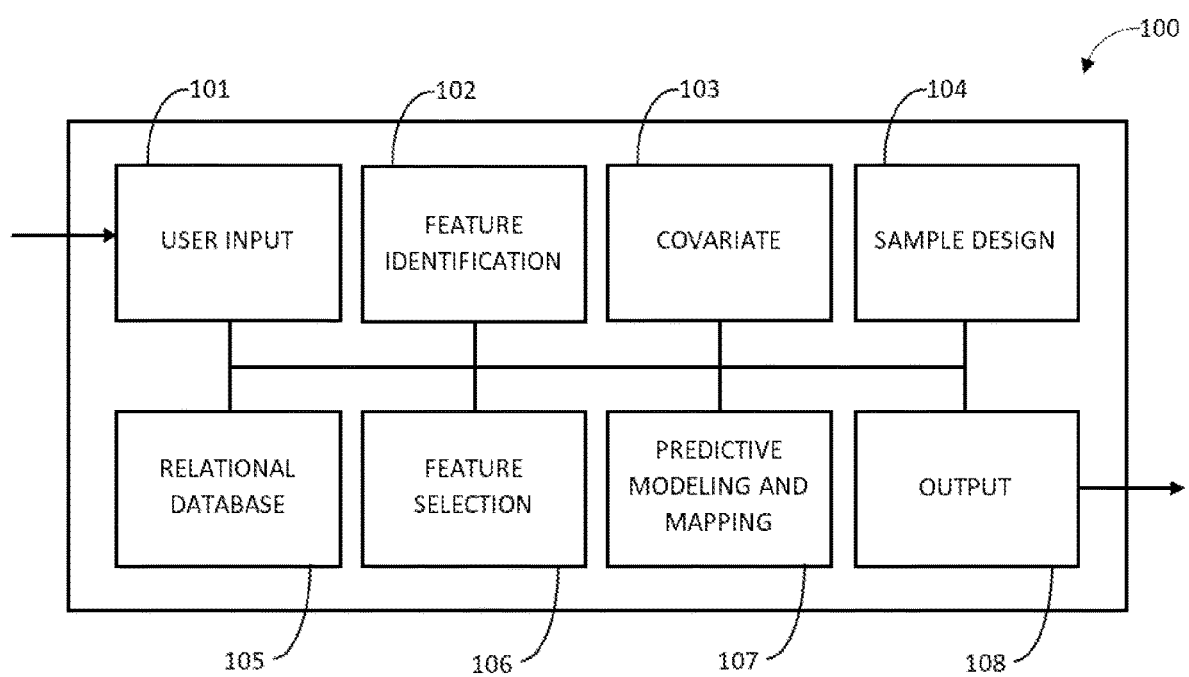
FIG. 1 is a block diagram illustrating aspects of functional elements and modules comprising an application for performing approaches to prediction which resolve soil map layers according to the present invention.

FIG. 1 is a is a block diagram illustrating elements and modules of a soil modeling and mapping framework 100. The soil modeling and mapping framework 100 is embodied in one or more systems and methods for creating optimized sampling designs, predicting soil properties based on such optimized soil sample designs, and for mapping soil properties such as soil fertility within a target field 209 at a geographical location 208 (referring to FIG. 2).

The soil modeling and mapping framework 100 analyzes input data representing a specific geographical location 208 that includes remotely-sensed data indicative of a landscape, terrain, contour, or topography of one or more fields at the geographical location 209, and one or more user inputs that include includes field management information relative to the geographical location 208. The remotely-sensed data may include one or both of satellite data, and ranging data, collected relative to the specific geographical location 208. Satellite data may include untransformed imagery from remote satellite-based sensing platforms, and ranging data may include transformed elevation data in remotely-sensed imagery, for example from LiDAR systems. Regardless of the type of input data, information contained therein is applied to a plurality of data processing elements or modules that are components within a computing environment that also includes one or more processors and a plurality of software and hardware components. The one or more processors and plurality of software and hardware components are configured to execute program instructions or routines to perform the mathematical functions, algorithms, machine learning, and other analytical approaches comprising the data processing functions described herein, and embodied within the plurality of data processing elements or modules. The plurality of data processing elements or modules may also include other elements or modules that are not herein illustrated; examples of such other elements or modules include databases which hold personal data provided to the company which is not relevant to the modeling and mapping processes, but for identifying the user of the framework 100.

The soil modeling and mapping framework 100 includes a user input module 101, also referred to herein is a data collection module, configured to ingest, receive, request, or otherwise obtain the input data from a plurality of different sources. Such sources may include user-related sources, or proprietary or third-party systems; regardless of the source, the input data as noted above may be comprised of information representing a geographical location 208 in some manner. This may include field-related information geo-referenced global position system (GPS) data, field and/or property boundary information, and any other information which may identify a field and its location on Earth. User inputs may include other site-specific information which may characterize a field(s) at the geographical location 208, including but not limited to spatially-related management data such as management plans, previously-configured management zones, landscape modification documents, etc. Such user-provided data may be used to improve overall system performance to enable more accurate predictions as patterns are discerned. The user input module 101 may be coupled with a specific database to relay any removed personal identification information among the user-provided data, so that such data may be anonymized for user protection.

The soil modeling and mapping framework 100 also includes a feature identification module 102, which may be configured to divide or parse a landscape of the geographical location 208 for the purpose of optimizing a sampling design 207, and for predictive modeling and mapping 107. The feature identification module 102 identifies large terrain features based on the environmental/topographical and land management characteristics. Spatially-related management information in the user inputs may serve to support a more accurate subdivision of the landscape. The soil modeling and mapping framework 100 includes, as noted herein, one or more applications of artificial intelligence and machine learning in the modeling functions performed therein, and at least elements 102, 103, 104, 106 and 107 may constitute a machine learning engine that is comprise of one or more layers or models of machine learning. One application of machine learning applied in the present invention involves techniques of unsupervised learning, which uses a combination of this information to identify large features for initializing soil sampling design. The feature identification module 102 may access a relational database 105 for retrieving user inputs such as identified or flagged landscape data that users of the invention have provided, or which have otherwise been ingested or obtained from other parties.

The soil modeling and mapping framework 100 also includes a covariate module 103, which is configured to manage sets of digital data collected from remote sensing platforms representing the landscape of the geographical location 208, and the functions to which those sets of digital data are applied. Covariates are parameters or variables that represent terrain derivatives that include, but are not limited to, digital hillslope position (DHP) models, digital elevation models (DEMs), and other digital representations of changes in terrain, and the sets of digital data itself may be derived and/or obtained from satellite remotely-sensed imagery, data sources producing derivatives of such remotely-sensed imagery, and imagery provided by unmanned vehicles or aircraft, commonly referred to as drones. Examples of data represented as digital terrain derivatives managed in this module include but are not limited to DHP, slope, profile curvature, stream-power index, etc. Examples of data derived from remotely-sensed data may include but are not limited to satellite imagery bands, and soil and vegetation indices (e.g., normalized difference vegetation index or NDVI, leaf area index, etc.).

A sample design module 104 in the soil modeling and mapping framework 100 manages the manner in which sample designs 207 are optimized for placement on a user's target site 209 in one or more field(s) at the geographical location 208. The module responsible for sample designs 104 receives input from the user input module 101, and applies one or more algorithms to design a customized sampling strategy for a new target site 208; features of the field(s) at this target site 208 are classified by defining features in the feature identification module 102 according to variables defined in the covariate module 103, to identify a plurality of optimized anchor points 403, with reference to FIG. 4. Optimized sample designs 207 from the sample design module 104 for these features are then projected for the new target field(s) 208 at the geographical location 209 according to these optimized anchor points 403. The complete set of these optimized anchor points 403 define the locations from which samples may be collected from the target sites 208 to generate data for the modeling and mapping of soil properties 107.

The sample design module 104 may access a separate database 105 for querying anonymized soil data provided, for example, by other users of the present invention (such as that for neighboring or similar fields, or even other users of the same fields at the geographical location 209). Such anonymized soil data may provide additional information that informs identification of optimized anchor points from selected features, and may also be stored in a database via the relational database module 105. Such anonymized user data may further include characterizations of users' soil landscape, regional information, and related land, crop and soil management information provided by users. Regardless, it is to be noted that the relational database module 105 serves to manage data storage, retrieval, and maintenance for analysis and support of other functions in the soil modeling and mapping framework 100.

The present invention also includes a feature selection module 106, which may be configured to manage decisions that result in dimensional reduction of resultants generated in the covariate module 103, for example to reduce overfitting of data and/or remove noise from such resultants. Methods may include regularization techniques (such as LASSO, elastic network, ridge regression, etc.) to prepare data for the modeling and mapping module 107. Both unsupervised and supervised learning algorithms may be applied in the feature selection module 106 to manage the output of the covariate module 103, based on successful predictions from past applications of a soil properties prediction model in modeling and mapping 107. By way of example, the feature selection module 106 may alter outcomes of the covariate module 103 where successful prior predictions of buffer pH (BpH) were resolved using medium range wetness index (MRWI) at 0.87 success consistency and a broad-range convergence index (BRCI) at 0.74 success consistency, such that MRWI and BRCI are promoted for future predictions of BpH. The stack of covariates (terrain derivates) generated in module 103 includes a large dimension of information that can increase the risk of overfitting. The feature selection module 106 decreases the risk of overfitting by application of one or more of the regularization techniques described above. This maintains the generalized nature of the modeling and mapping module 107 for future applications.

The present invention also includes a modeling and mapping module 107, which may comprise elements of both a machine learning modeling engine and a mapping engine within the framework 100. The modeling and mapping module 107 is configured to predict soil properties based on the optimized, customized soil sample design 104, and map soil properties at the target site 208. The modeling and mapping module 107 may apply many models of artificial intelligence and machine learning (e.g., neural networks, bagging, boosting, etc.), which may further include, but are not limited to, random forest, boosting, artificial neural networks, convolution neural networks, etc., at least as to the modeling functions performed therein. The modeling and mapping module 107 uses supervised learning models to discover a mapping function to predict the output variable(s) (from collected soil information in module for sample design 104) with input variable(s) (from collected information in covariate module 103). Output maps are produced by translating the regression output from machine learning models to spatial data layers using appropriate covariates generated in the covariate module 103 and selected in the feature selection module 106.

The soil modeling and mapping framework 100 may also include an output module 108 which is configured to act as realization element for export of information as output data in various use cases of the present invention, such as for example an interface for visualization of the predictions and maps generated by the modeling and mapping module 107. File formats of the output data generated by this output module 108 include, for example, "SHP", "GTIF", "TIFF", "JPG", "JPG2000." Many other file formats are also possible, and are within the scope of the present invention. Files may also be modified within a localized geographic information system to perform secondary calculations to generate specific value-added products including but not limited to nutrient recommendation maps, and amendment recommendation maps. The output module 108 may also house basic analysis and overlay tools. The output module 108 may be further configured to generate instructions for actions to be taken in response to maps of soil properties, such as an application of a soil treatment at the target site 208 that comprises a management zone, where a user performs the soil treatment according to a map, or an automated soil treatment is controlled according to the map. Output module 208 may therefore also be configured to generate instructions that can be interpreted by hardware and software elements on board agricultural equipment to carry out such treatments.

Example of Soil Sampling

Figure 2:
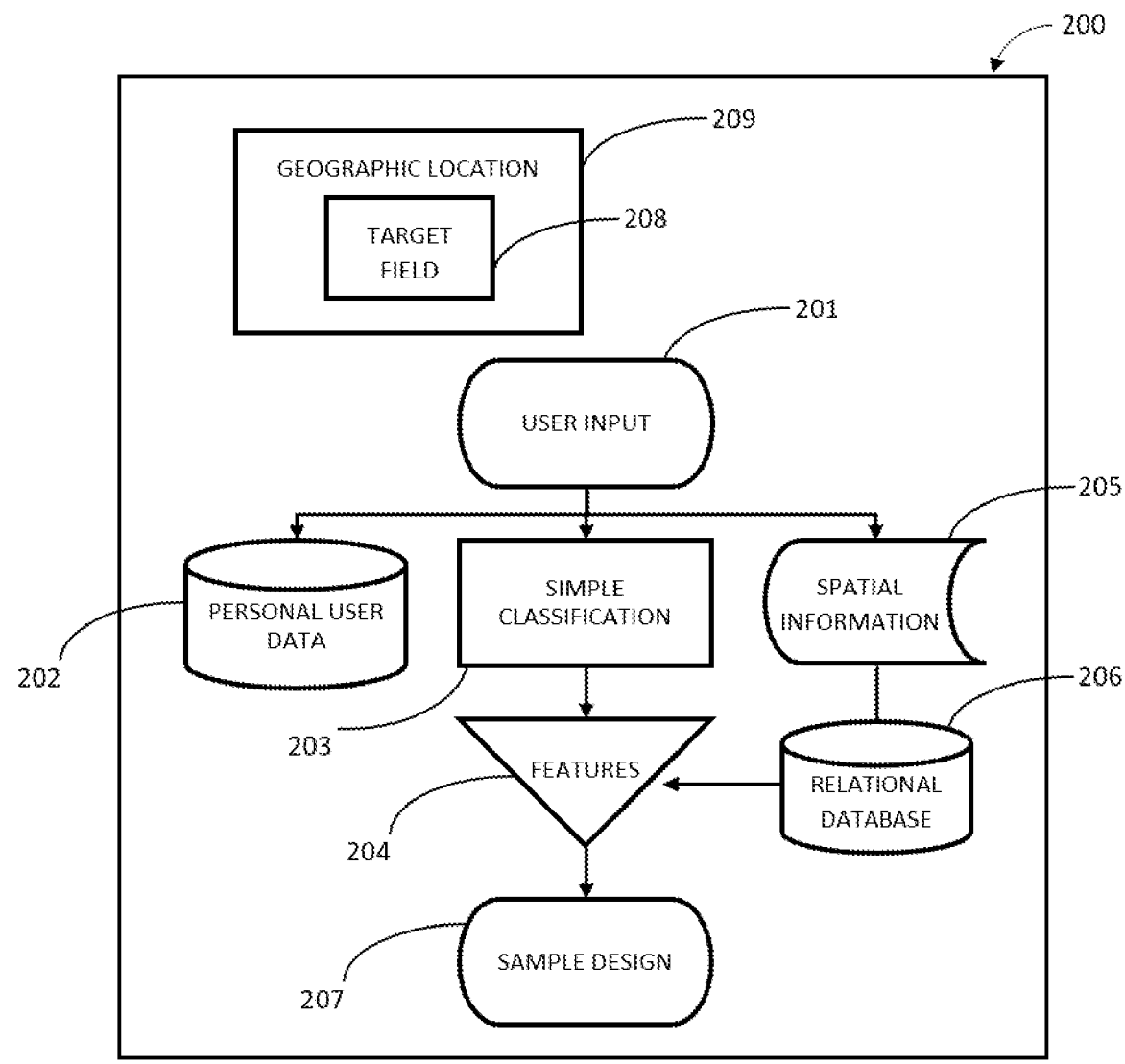
FIG. 2 is a flowchart illustrating the soil sampling method according to the present invention.

FIG. 2 is a flow chart illustrating an exemplary process 200 for creating a customized sampling design 207 within the soil modeling and mapping framework 100. The systems and methods embodied in this exemplary approach generate soil parameters for similar soil-forming environments, where a user is able to share a portion of that user's soil information with other users. Inclusion of such soil-forming environments may be a programmed function of the soil modeling and mapping framework 100 that enables such sharing of soil parameters to improve the predictive modeling and resultant mapping as outcomes of the present invention. The soil modeling and mapping framework 100 may therefore utilize information shared by users in selecting features for predicting soil properties in a target geographical location.

Figure 4:
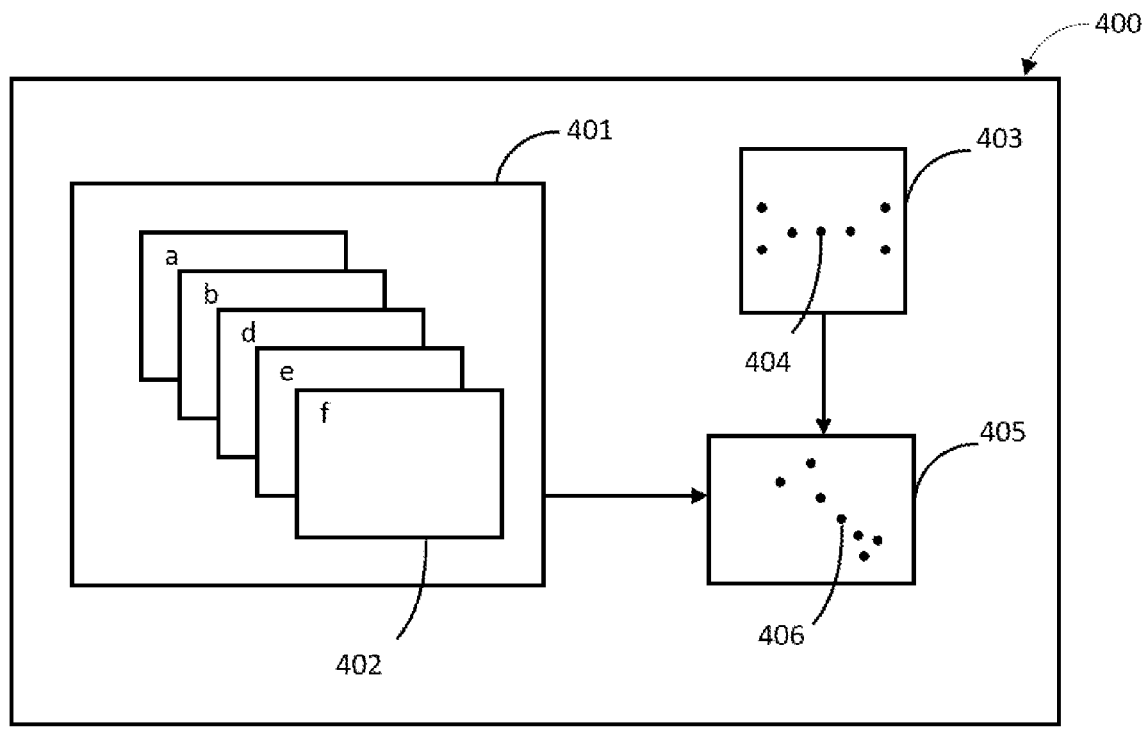
FIG. 4 is a diagram illustrating a sampling strategy defined by several layers of input variables a, b, d, e, and f, according to the present invention.

FIG. 4 is a flow chart illustrating the determination of a soil sampling design for a target field(s). A stack of covariates 401 (a, b, d, e, f) is used to represent a feature on the target field 208, at a geographic location 209. An individual covariate 402 captures a variability of a landscape (further described in equation (1)). Reference numeral 403 is an ideal sample design for a particular class of geographic feature.

One such location in the ideal sample design 403 is used as an anchor point 404. An anchor point 404 is used to project the ideal sample design 403 to the target field 208 at a particular geographic location 209. The as-applied sample design 405 is a projection of the ideal sample design 403 with the anchor point 406 on the target field 208 at a geographic location 209.

A user input 201 contains information that is useful for identification of the user, as well as any qualifying information about a target site 208 for which soil information is being provided. Personal user information is removed from workflow involved in arriving at the customized sampling design 207 in the process 200; a record is added to a separate personal user database 202 and stored in memory. Spatial information 205 about the target site 208 (including but not limited to location, artificial drainage, wet spots, as in 304 and 305 in FIG. 3) is added to records in a relational database 206 and held in memory. These are identified as potential soil-forming environments. Digital representations of the target site 208 are used to classify the field identified from user data in simple classification 203. The present invention queries its own records of soil landscape features for those that align with the information input by the user. All features 204 identified across the landscape of the target site 208 are merged with redundant features removed from the sample design space. Sample designs 207 are anchored to the landscape following various patterns in a confluence of digital representations of the landscape 401 as illustrated in FIG. 4. For example, a field may be classified into individual features. Select digital representations (individual covariates) 402 from the complete set in the stack of covariates 401 are used to classify the feature. In this example, it is labeled "100m_hill." The present invention queries for an ideal soil sample design 403, one of which would be used to sample hill features. The present invention determines the most ideal examples of "100m_hill" on the target field 208 as defined in the spatial information 205 in the database 206. The present invention keeps that instance of "100m_hill" for its customized sample design 207. A pattern of optimized, ideal soil sample locations 403 is then projected from the ideal hill to the example "100m_hill" from the target site 208 to be mapped in the as-applied sample design 405 matching the anchor points from ideal hill 404 and "100m_hill" at anchor points 406.

Figure 3:
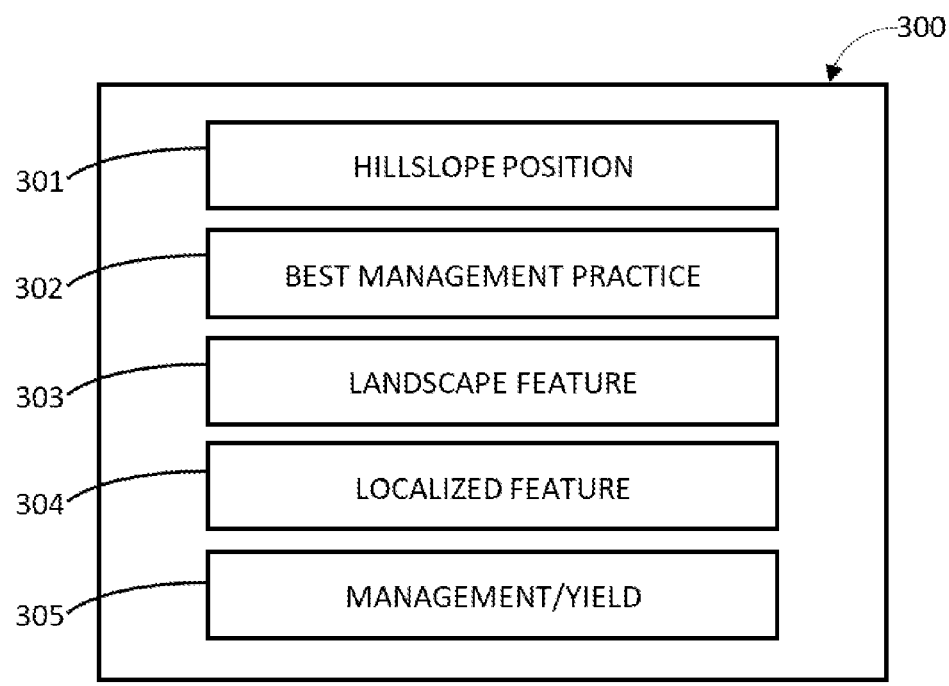
FIG. 3 is a diagram illustrating various parameters used in site definition according to the present invention.

Sample designs 207 are then mosaiced with features labeled from feature classifications accordingly, and according to the process 300 illustrated in FIG. 3. For example, this may include alignment with edges and centers labeled in such feature classifications. Soil information from optimal soil sampling locations then determines the best relationship (pattern match) between soil information and the environmental features in those classifications. Such a pattern may therefore be applied to predict soil properties across entire landscapes of the target site 208.

Soil Mapping Techniques

As noted throughout, one application of the present invention is mapping of predicted soil properties such as soil fertility. Customized sampling designs 207 that are created within the soil modeling and mapping framework 100 enable three mapping techniques—internal, rolling (semi-trained), and external. Each of these mapping techniques utilize different degrees of involvement with regard to data collection in the customized sampling design 207. The difference between the applicability of these mapping techniques occurs in part due to the complexity of the landscape, as well as in the amount of classified data available.

The internal or sampled technique selects a collection of soil samples to provide soil information based on the customized sample design 207 occurring in sample design module 104 in FIG. 1, and generated as sample design 207 in FIG. 2, and further described herein. This approach is considered to employ a "sampled" site to predict and map soil properties from samples taken across the landscape of the target site 208.

The rolling, semi-trained or semi-sampled technique employs a reduced number of collected samples based on the customized sample design 207 occurring in sample design module 104 in FIG. 1, and generated as sample design 207 in FIG. 2, and further described herein. This approach is considered to employ a "semi-sampled" site to predict and map soil properties across the landscape. The database 206 may comprise a collection of soil information from related, already-sampled locations, such as those with similar landscape features as the new field at the target geographical location. Within this technique, the invention trains itself by flagging records and classifying sample data's spatial relationships in spatial information 205.

Using the rolling or semi-sampled technique, the present invention creates soil property maps across a field(s) at a target site 208 using a limited number of samples collected. The database 206 compensates for missing features using relationships previously learned from the prior predictions. For example, if the user submits a target field for mapping that has knoll on the landscape, the sample design process may not sample the knoll feature, instead, using older records of knolls stored in the database which relate to the instance. Soil samples may be placed on other unknown features on the target site 208. Such features' spatial information 205 would be extracted and learned for future use.

In the external or unsampled technique, the present invention generates maps of soil properties across a field at a target site 208 without having any soil samples. The present invention uses the collected soil information already stored in the database 206 (collected soil information from already sampled or semi-sampled field) that share similar landscape elements. The external method is an extension of the principles of the rolling model, but leverages existing information for all features that comprise the target site 208. For example, a user has a field to be mapped which contains a drumlin, a few other features, and is otherwise unremarkable. A complete sample strategy is not composed to represent the drumlin and waterway; external information is leveraged to identify the range of the target feature the drumlin occupies. The present invention supplements all samples from its database; already-known examples are projected and anchored to the target site 208 and soil properties are calibrated and assumed to be true by the modeling and mapping module 107. This process is repeated for the other features at this target site 208 which are already understood, and this compiled dataset is used as inputs for the modeling and mapping module 107.

FIG. 3 is a diagram illustrating a process 300 in which various variables or parameters used in site definition identify landscape features. FIG. 3 illustrates criteria for quantification of soil-formation environments to capture the functional variability of the landscape in such a process 300, to enable selection of soil sampling locations for predicting soil properties in target field(s) 208. Organization of these variables or parameters may be based at least in part on the ability to identify such variables or parameters relative to the target field 208 for which the soil modeling and mapping framework 100 is applied.

One such variable or parameter is hillslope position 301, which provides a landscape geometry profile derived from conceptual digital hillslope position models for soil landscapes. Any hillslope is defined by three components: gradient, slope length geometry, and slope width geometry. A two-dimensional profile of a hillslope positions divides into five components: summit, shoulder, backslope, footslope, and toeslope. Goals of hillslope positions 301 derived from digital hillslope position models include representing the role of slope, water dynamics, soil erosion, and deposition.

Another variable or parameter is best management practices (BMPs) 302, which are engineered solutions for biological systems with the goal of preserving water quality. Goals of BMPs 302 include controlling erosion and sedimentation on agricultural and industrial sites. Examples of BMPs 302 include but are not limited to animal trails & walkways, fences, grassed waterways, and constructed wetlands. As BMPs 302 are engineered solutions, their presence changes soil formation, transformation, and function, and knowledge of these variables or parameters influences predictions of soil properties.

Landscape features 303 are another variable or parameter, and include features of the broader geographic landscape, such as for example foothills, rivers, valleys, and moraines. Still a further variable or parameter to be considered include localized features 304. These describe features that exist within users' field boundaries. These features may or may not be identified by existing surveys. Examples include but are not limited to sand pits, ditches, and wells.

Management/yield 305 is another variable or parameter, and includes external sources of information that the user provides that further characterize the target field 208 in the soil modeling and mapping framework 100. External information may include, but not limited to seeding rates, and yield from previous seasons' harvests.

The following equation may be utilized in the present invention to capture the variability of the landscape across a particular field:

$$y(i,j) = x1(i,j) + x2(i,j) + x3(i,j) + x4(i,j) + x5(i,j) \quad (1)$$

where y(i,j): predicted the variation of the landscape at location (i,j)

x1 (i,j): landscape geometry as defined by DHP at location (i,j)

x2 (i,j): involved best management practices at location (i,j)

x3 (i,j): involved landscape features of the target field(s) at location (i,j)

x4 (i,j): shared locally-existing information at location (i,j)

x5 (i,j): involved yield information at location (i,j)

In equation (1), y(i,j) describes predicted variability of a particular location. A measure of variability may be calculated for each location of a field for a season, and may vary depending on variables or parameters such as those indicated in FIG. 3.

x1 (i,j) describes landscape geometry defined by DHP (digital hillslope position) of a particular location. DHP is a model used by soil scientists when describing soil formation, translocation, and transformation. Standardized classification, or DHP, can be used to describe rates of change of soil across a landscape. At a particular location (i,j), DHP is used in confluence with other locations to define landscape variability.

The presence of active site modifications as represented by x2 (i,j) are Boolean in nature, modified or not modified, and count towards the number of features needed to create sample designs, particularly when implementing the rolling (semi-sampled) method for mapping. Variability from best management practices is generally standard, as they are engineered for a particular function.

x3 (i,j) describes landscape features at a particular location (i,j). These objects, as natural features, contribute variability from their current and past geometry. For this reason, the amount of variability they contribute is relatively greater than x2 (i,j) but they may be managed by classification with other similar landscape features.

x4 (i,j) describes local information collected which defines the range of total variability of a region. This may be defined by major land resource areas, watersheds, or on a more local scale communities of individual agronomists and/or farmers. This source of variability references Tobler's First Law of Geography, "everything is related to everything else, but near things are more related than distant things."

x5 (i,j) describes variability observed by yield. Yield is a functional summary of biological activity on commercial farmland. Higher yield in one location on the landscape relates to soil available nutrients and conducive soil environments. Particular locations (i,j) do not yield at the same rate as their neighbors. Magnitudes in differences in yield directly relates to soil so this source of information may be used to quantify soil variability at locations in field.

Unlike conventional soil mapping processes, the present invention utilizes remotely-sensed information to guide soil sampling locations for predicting and mapping soil properties. The present invention may be implemented in conjunction with any of the following environmental features: satellite imagery bands, soil and vegetation indices, terrain derivatives, etc., for selecting soil sampling locations and mapping soil properties on sampled or unsampled locations.

FIG. 4 is a graphical illustration 400 of how a sample design is determined, given the availability of different collections of data. The soil modeling and mapping framework 100 considers multiple layers of relevant data 401. Reference numeral 402 is an individual spatial layer that represents a processed set of the relevant data 401, including for example processed digital terrain models (e.g., NDVI) and raw data (e.g., Landsat 8 band, Sentinel2 band). For example, one or more machine learning models are applied to classify the target site 208 into multiple classes based on input data (the multiple layers of relevant data 401). Then, the one or more machine learning models are further applied to select soil sampling locations within defined classes to cover the feature space of the landscape. Anchor points 404 for soil sampling locations are then defined based on the complexity of the multiple layers of relevant data 401. The present invention selects soil sampling locations for the customized soil sampling design based on the complexity of landscape, and not necessarily geographic area, to capture the soil variability of that landscape.

Example—Soil Mapping Using Proposed Soil Sampling Design/User-Supplied Data

The systems and methods of the present invention described herein may be performed using the customized sampling design 207; in an alternate embodiment, they may also be performed using user-provided spatial data. Users may therefore create maps using the customized sampling designs 207, or create maps using their own spatially-relative collected data. It is therefore to be understood that mapping portion of the inventive concept described herein may be performed in different ways.

Figure 5:
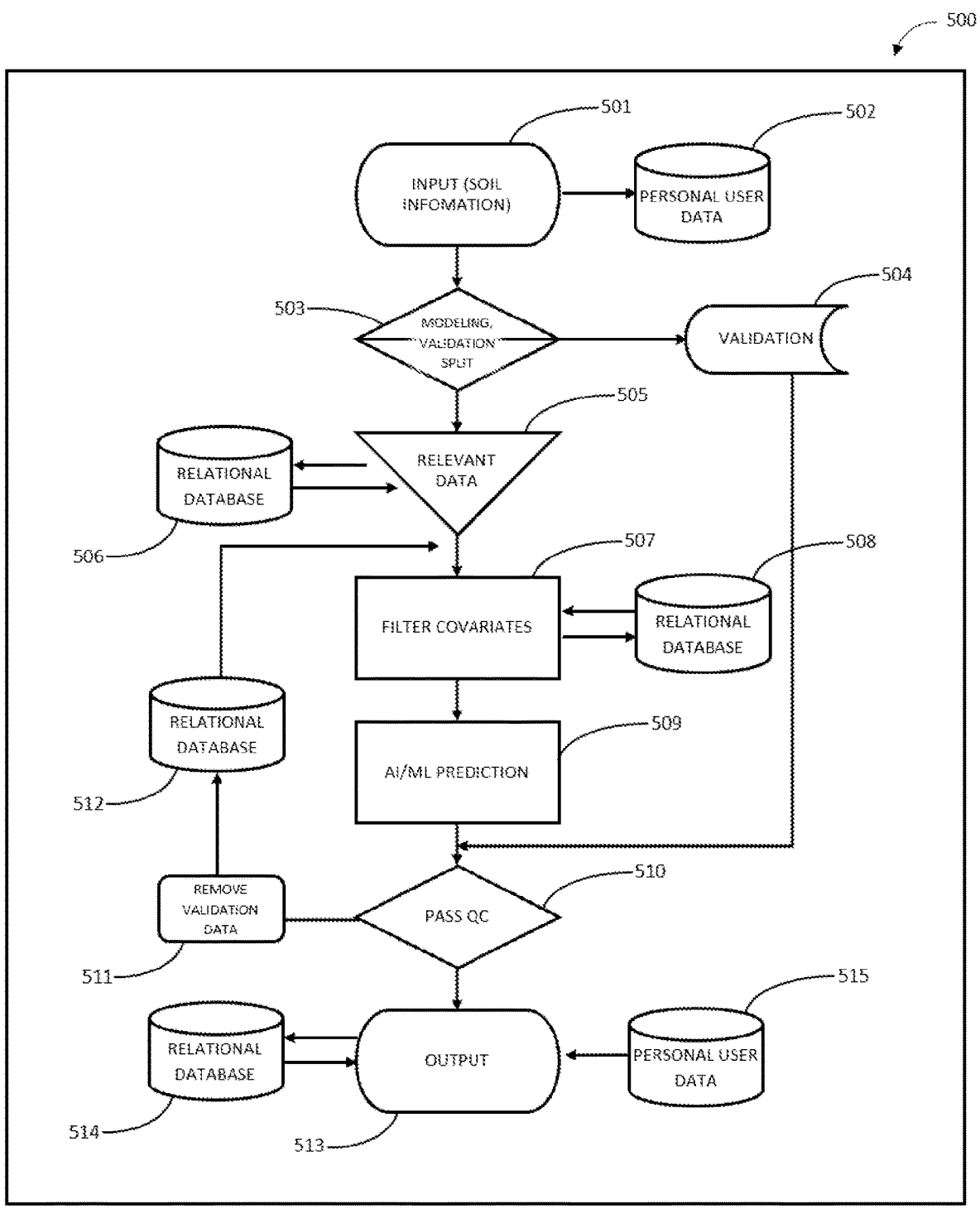
FIG. 5 is a flowchart illustrating an exemplary approach to modeling of soil data to predict and map soil properties, according to the present invention.

FIG. 5 is a flow chart illustrating an exemplary approach to spatial prediction and mapping 500 of soil properties, according to one embodiment of the present invention. Input data in the form of geo-referenced soil information 501 is ingested into the system, for example in a file format such as "GPKG", "SHP", "CSV", "TXT" or any other suitable file format. This input data may be cleaned in a pre-processing step (not shown), to remove inconsistencies, correct/harmonize units, etc., to prepare it for the modeling steps discussed below. Personal user data 502 is removed during this process; a record of such information may be added to a separate database, and a copy stored in memory, if needed. Cleaned, pre-process input data is modeled and parsed to reflect the sample's feature spaces from sample data collected according to the sample design 200 as described above with respect to FIG. 2, at step 503. Validation data 504 is removed from the modeling performed in module 503, and stored in memory to be reintroduced after the machine-learning prediction module 509 is performed. Relevant data 505 is added from a relational database 506; this relevant data 505 supports the features identified by the customized sampling design 200, assuming that the user has features at the target site 208 that are classified similarly to data already stored in the relational database 506.

Referring back to FIG. 1, the approach of FIG. 5 uses a large number of data layers to create high-quality soil property maps. To avoid overfitting and decrease computation time, the present invention filters covariates 507 using one or more regularization techniques to further select features 106 as in FIG. 1. Examples of regularization techniques may include, but are not limited to, L2 and L1 Regularization, dropout, early stopping, and data augmentation. In the invention, regularization techniques are supervised machine learning models which find the best relationship between the target variable (soil property in the sample design 104) and environmental information (stack of covariates 103). Relationships are then identified and used to characterize the soil environments across landscapes at a target site 208.

Outcomes from application of the regularization techniques for each soil property at the target site 208 are listed and stored in a relational database 508. Each entry edits a weighting system for feature selection that occurs in other cycles of the present invention. Learning is referenced upon performance of iterations, if and when they occur.

An adaptive covariate stack may be defined by a modified stack of filtered covariates 507 to be used by the machine learning-based predictive modeling 509, by learning from prior instantiations of such modeling of soil predictions. Data is queried from successful cycles of prior soil predictions (stored, for example, in database collections 512, 514) and added to selected features in the stack of filtered covariates 507 in the event that regularization techniques used do not produce strong results. As more prediction cycles are completed and more data are accumulated, the more effective the adaptive covariate stack will be at assembling itself.

If there is not enough information to support the generation and application of an adaptive covariate stack, a naïve covariate stack may be used. A naïve covariate stack is defined as a predetermined stack of covariates to be used by predictive modeling 509, comprised of a standard sample of all features present in the covariate stack.

The machine learning-based prediction of soil properties 509 is performed using the stack of filtered covariates 507 that determined to be the most relevant for a successful prediction as predictors, following application of non-block machine learning algorithms to learn the process of training, and then other machine learning algorithms to reach to the desired performance. For example, the target site 208 is divided into regions using data from the stack of filtered covariates 507. A machine learning algorithm determines the best pattern/relationship between a target variable (a soil property) and predictors (environmental features from the stack of filtered covariates 507). To complete the prediction, the invention applies the discovered pattern to the rest of the unsampled locations of the landscape to map soil properties spatially by coverage from variables in the stack of filtered covariates 507.

Results are then applied to a quality control module 510 where validation data 504 is re-joined with the results of predictive modeling 509 to evaluate performance. If results do not pass a pre-defined quality threshold, the predictive modeling 509 may be repeated. In such further iterations, validation data 504 may be removed from the dataset at step 511 and performance metrics saved to a relational database 512 for learning. Hyperparameters which impact feature selection of filtered covariates 507 may be changed, and the cycle repeated. In the iterations, a different feature selection method will be used, e.g., a different regularization configuration, (adaptive contingency or naïve contingency). Once an outcome is reached that passes the pre-defined quality control threshold, the approach to spatial prediction and mapping 500 creating maps of predicted soil properties at step 513, and selects the desired/appropriate spatial resolution to create practical management zones for map users. This represents an output of the approach to spatial prediction and mapping 500; data represented such maps may be stored at a database 514, and any necessary user personal data may be added back at step 515 to improve the output, for example as a presentation of the mapping 513.

Figure 6:
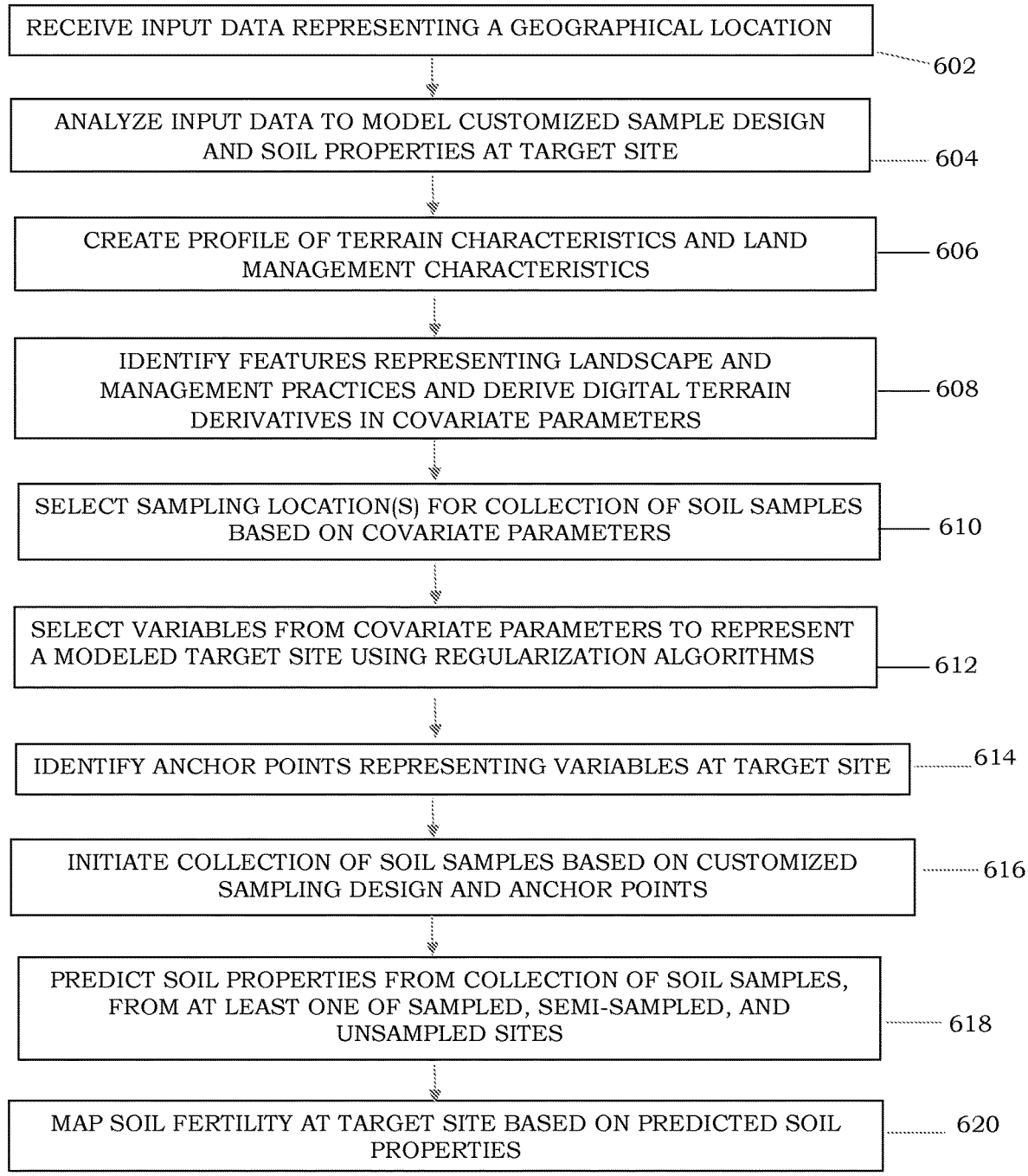
FIG. 6 is a flowchart of steps performed in a process for soil modeling and mapping using customized sample designs according to one embodiment of the present invention.

FIG. 6 is a flowchart illustrating steps in an exemplary process 600 for performing the soil modeling and mapping framework 100, according to one embodiment of the present invention. At step 602, input data representing a geographical location 209 is received and initiated for processing within the machine learning modeling engines and mapping engines described herein, and at step 604, the process 600 begins analyzing the input data to characterize the landscape of the geographical location 209 to determine locations for taking soil samples in a customized sample design 207, and model soil properties at a target site 208 based on the customized sample design 207.

At step 606, the process 600 creates profile of terrain characteristics and land management characteristics, and at step 608 identifies features representing landscape and management practices; these may include, as noted above, features that represent characteristics such as hillslope position, landscape features, localized features, and yield land management information for the geographical location. The process 600 then applies one or more machine learning models to derive digital terrain derivatives in a stack of covariate parameters, where the one or more digital terrain derivatives represent changes in elevation and contour in the landscape across a target site 208 at the geographical location 209. The process then selects one or more soil sampling locations for a collection of soil samples based on those covariate parameters at step 610.

Variables are then selected at step 612 from the covariate parameters to represent a modeled target site 208, using regularization algorithms to reduce over-fitting and minimize the effect of noise and other error in the dataset. At step 614, the process 600 then identifies anchor points 403 representing variables at the target site 208, and arrives at a customized sampling design 207 based on the landscape of the geographical location 209. At step 616, a collection of soil samples is initiated based on the customized sampling design 207 and the anchor points 403.

At step 618, the process 600 applies further machine learning models to predict soil properties from the collection of soil samples, from at least one of sampled, semi-sampled, and unsampled sites, at step 620, maps predicted soil properties such as soil fertility at the target site 208, based on predicted soil properties and according to one of the mapping techniques of internal, rolling, or external, as determined at least in part by the amount of samples taken.

Use Cases of Mapping of Soil Properties

Maps created according to the present invention may be used in a number of ways. For example, as noted above, maps be utilized to identify and define management zones, and these may be used for applications of soil fertility treatments and/or otherwise managing soil conditions (such as identifying treatments or biological processes to be applied to soils, and at particular locations in a target field). They may also be used for follow-on modeling such as predicting crop yield, and potential dates for planting and harvesting, as well as for off-season activities such as tillage.

Soil maps may also be used initiate treatments such as soil fertility treatments using agricultural equipment, and the present invention may be configured to generate instructions for performing such treatments, including instructions that can be interpreted by software and hardware elements for automated control of such equipment to perform activities within agricultural fields.

Further Discussion of Application of Machine Learning Layer(s)

As noted throughout, layers of artificial intelligence and machine learning may be applied in the present invention at least three different areas: identifying areas of a landscape for sample collection to arrive at the customized soil sampling design, data preparation/organization/image processing for the modeling and mapping of data collected according to a customized sampling design, and modeling/interpolation of data to predict soil properties. Each of these areas utilized particular types of machine learning algorithms, according to specific needs for evaluating data.

Regardless of where it is applied and to what particular function in the soil modeling and mapping process and framework 100, the data analysis and modeling performed in these one or more layers of machine learning may comprise many different types of machine learning, and apply many different mathematical approaches to analyzing information and generating outputs that improve outcomes of the various functions described herein.

The one or more layers of machine learning may be comprised of any of several different mathematical approaches, as noted above. These may include statistical analyses, which are non-deterministic mathematical approaches that enable calculation of probabilities that events will or will not occur. In a statistical model specified via mathematical equations, some of the variables do not have specific values, but instead have probability distributions, so that some of the variables are stochastic or random; in other words, such models examine approaches that involve variables whose values depend on outcomes of random phenomena. Statistical analyses may be applied in the present invention to examine probabilities of different future outcomes, such as the probability that the price of a financial instrument will reach a desired level at a specified future time, given certain variables, some of which have random or uncertain values. Such statistical analyses may be applied either alone, or in conjunction with, other machine learning approaches.

This invention uses both supervised and unsupervised learning. Supervised learning can broadly be classified into regression and classification learning models. These models are applications of mathematical functions in algorithms that classify input data to find specific relationships or structures therein that allow the machine learning prediction engine to efficiently produce highly accurate output data. There are many types of such algorithms for performing mathematical functions categorized as supervised learning approaches. Examples include regression analysis (including the logistic regression discussed above, and polynomial regression, and many others), decision trees, Bayesian approaches such as naive Bayes, support vector machines, random forests, anomaly detection, etc.

Regression analyses are types of statistical analyses where models are used for estimating the relationships between variables of interest, such as for example a dependent variable and one or more independent variables (often called 'predictors'). This type of machine learning is used to infer causal relationships between the independent and dependent variables, and for prediction and forecasting of outcomes where such causal relationships are impactful on future states for application of the overall modeling being performed. There are many types of regression analyses, such as linear and non-linear regression, and specific approaches such as logistic regression, that enable the use of derived parameters, such as indicators in technical analyses, to interpret the importance of maximum values in form of the log-odds when calculating probability values. For example, other types of logistic functions, and other types of regression analyses, may also be utilized to calculate probabilities in the present invention, and are within the scope of the present invention. Other approaches that may be utilized include, but are not limited to, decision trees, random forest classifiers, support vector machines, and probit. It is therefore to be further understood that the present invention, and the present specification, are not to be limited to any one type of mathematical model or statistical process mentioned herein, particularly as to its application in the one or more layers of machine learning.

Machine learning modeling may also include, as noted above, applications of neural networks. Neural networks generally are comprised of nodes, which are computational units having one or more biased input/output connections. Such biased connections act as transfer (or activation) functions that combine inputs and outputs in some way. Nodes are organized into multiple layers that form the neural network. There are many types of neural networks, which are computing systems that "learn" to perform tasks, without being programmed with task-specific rules, based on examples.

Neural networks generally are based on arrays of connected, aggregated nodes (or, "neurons") that transmit signals to each other in the multiple layers over the biased input/output connections. Connections, as noted above, are activation or transfer functions which "fire" these nodes and combine inputs according to mathematical equations or formulas. Different types of neural networks generally have different configurations of these layers of connected, aggregated nodes, but they can generally be described as an input layer, a middle or 'hidden' layer, and an output layer. These layers may perform different transformations on their various inputs, using different mathematical calculations or functions. Signals travel between these layers, from the input layer to the output layer via the middle layer, and may traverse layers, and nodes, multiple times.

Signals are transmitted between nodes over connections, and the output of each node is calculated in a non-linear function that sums all of the inputs to that node. Weight matrices and biases are typically applied to each node, and each connection, and these weights and biases are adjusted as the neural network processes inputs and transmits them across the nodes and connections. These weights represent increases or decreases in the strength of a signal at a particular connection. Additionally, nodes may have a threshold, such that a signal is sent only if the aggregated output at that node crosses that threshold. Weights generally represent how long an activation function takes, while biases represent when, in time, such a function starts; together, they help gradients minimize over time. At least in the case of weights, they can be initialized and change (i.e., decay) over time, as a system learns what weights should be, and how they should be adjusted. In other words, neural networks evolve as they learn, and the mathematical formulas and functions that comprise neural networks design can change over time as a system improves itself.

The application of neural networks within the soil modeling and mapping process and framework 100 may include instantiations of different networks for different purposes. These include both "production" neural network(s), configured to refine the algorithms performed within the overall modeling framework to generate output data, and "training" neural network(s), configured to train the production network(s) using improvements on the reasons for prior, historical outcomes of predictions or forecasts that have been learned.

The components of such a specially-focused neural network form its internal state and include a cell, which acts as the memory portion of the block, and three regulating gates that control the flow of information inside each block: an input gate, an output gate, and a forget gate. The cell remembers values over arbitrary time intervals, by keeping track of the dependencies between elements in an input sequence, and the three gates regulate the flow of information into and out of the cell. The input gate controls the extent to which a new value flows into the cell, the forget gate controls the extent to which a value remains in the cell, and the output gate controls the extent to which the value in the cell is used to compute the output of the block. The decision-making function of these gates is often referred to as the logistic sigmoid function for computing outputs of gates in these types of neural networks. There are connections into and out of these gates, and at least the weights of these connections, which need to be learned during training, determine how the gates operate.

Inside neural network blocks, there are additional layers that perform the activation functions needed to ensure that time-dependent data sequences are properly analyzed to avoid decay. One such activation function that may be incorporated is a tan h layer, which effectively classifies input data by determining which input values are added to the internal state of the block. Input gates are a layer of sigmoid-activated nodes whose output is multiplied by inputs classified by preceding tan h layers. The effect of these activation functions is to filter any elements of the inputs that are not required, based on the values assigned to each node for the problem being analyzed, and the weights and biases applied. The weights applied to connections between these nodes can be trained to output values close to zero to switch off certain input values (or, conversely, to pass through other values). Another internal state of a block, the forget gate, is effectively a feedback loop that operates to create a layer of recurrence that reduces the risk of decay in time-dependent input data. The forget gate helps the neural network learn which state variables should be "remembered" or "forgotten".

Neural networks are also a type of such supervised learning approaches, which may also include one or more of the computational techniques in the algorithms described above within their structures. Neural networks are more flexible than regression approaches, and allow for combinations of both structured data (e.g., sensor data) and unstructured data (e.g., observations discerned from user observations) as inputs to produce the types of outputs desired.

API Elements

Access to the soil modeling and mapping process and framework 100 of the present invention may be provided through one or more application programming interfaces (APIs). The present invention contemplates that many layers of APIs may be utilized, for example to enable ingestion of particular forms of input data, or customized uses of the predictive output data. APIs may be managed by an API element specifically configured for each implementation thereof, for example as a specific sub-element of a data collection element within the plurality of data processing elements for intake of certain types of information that require a particular format or conversion from a particular format. The data collection element may itself be thought of as a layer of APIs configured to ingest input data.

APIs may also be utilized for creating and displaying dashboards of information, for example of an operational status of an external system controlled by the machine learning-based modeling platform. A further layer of APIs may be provided for output data, such as issuing instructions or commands to initiate an actionable event or actuate an external system following a prediction of soil properties made within the machine learning-based modeling performed in the soil modeling and mapping process and framework 100. Third party systems may also utilize APIs within the present invention to develop their own, follow-on uses of the predictions generated by the machine learning-based modeling, such as to generate and export customized reports, comply with regulatory requirements, generate recommendations, risk assessments, or alerts, or develop their own enterprise-specific applications.

It is to be understood that the systems and methods of the present invention may be implemented in many different computing environments. For example, in addition to being operable within a completely cloud-based environment, the coordinate management framework may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, and any comparable means. In general, any means of implementing the methodology illustrated herein can be used to implement the various aspects of the coordinate management framework. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors), memory, nonvolatile storage, input devices, and output devices. Furthermore, alternative software implementations including, but not limited to, distributed processing, parallel processing, or virtual machine processing can also be configured to perform the methods described herein.

The systems and methods of the present invention may also be partially implemented in software that can be stored on a non-transitory storage medium, executed on programmed general-purpose computer with the cooperation of a controller and memory, a special purpose computer, a microprocessor, or the like. In these instances, the systems and methods of this invention can be implemented as a program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, artificial intelligence, fuzzy logic, expert system or combination of hardware and software that is capable of performing the data processing functionality described herein.

The foregoing descriptions of embodiments of the present invention have been presented for the purposes of illustration and description. It is not intended to be exhaustive or to limit the invention to the precise forms disclosed. Accordingly, many alterations, modifications and variations are possible in light of the above teachings, may be made by those having ordinary skill in the art without departing from the spirit and scope of the invention. For example, a target site 208 may or may not be the same site as a geographical 209; instead, the target site 208 may be an area having the same or similar terrain and field characteristics and land management characteristics. It is therefore intended that the scope of the invention be limited not by this detailed description. Further, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. A method, comprising:
   receiving input data representing a geographical location, the input data including remotely-sensed data indicative of a landscape of the geographical location, and user input information that includes field management information relative to the geographical location;
   analyzing the input data to characterize the landscape of the geographical location to determine locations for collecting soil samples in a customized sample design and model a soil-forming environment of and map soil properties at a target site based on the customized sample design, by:
   developing a soil-formation model for simulating seasonal soil formation and development at the target site, and organizing a plurality of soil-related data layers representing a soil-forming environment of the target site, the soil-formation model developed by:
   creating a profile of terrain characteristics and land management characteristics, by identifying features that represent hillslope position, landscape features, localized features, and yield land management information for the geographical location,
   applying one or more machine learning-based models to derive one or more digital terrain derivatives in covariate parameters, the one or more digital terrain derivatives representing changes in elevation and contour of the landscape across the target site, and select one or more soil sampling locations for a collection of soil samples based on the covariate parameters,
   selecting one or more variables from the covariate parameters to represent the target site in the plurality of soil-related data layers, by applying one or more regularization algorithms to reduce over-fitting in the stack of covariate parameters,
   identifying one or more qualified sample points in the customized sample design from a confluence of one or more spatial models of digital representations of the soil-forming environment in the plurality of soil-related data layers at the target site for one or more simulations by the soil-formation model, wherein the customized sample design identifies qualified sites within the target site from the one or more qualified sample points along with spatially-paired helper sampling locations identified at least from a digitized hillslope position at the target site; and predicting one or more soil properties from the collection of the soil samples for sampled and unsampled sites at the target site; and mapping soil fertility at the target site based on predicted soil properties of and associated soil test data within the sampled and unsampled sites, wherein the collection of the soil samples is from qualified sites identified by the one or more qualified sample points at the target site, and a user performs the collection according to the customized sample design, or an automated collection is controlled according to the customized sample design, and wherein the predicting the one or more soil properties and the modeling and mapping of the soil fertility occur where both soil samples have been collected and where no soil samples have been collected, and wherein agricultural equipment is automatically controlled to spatially treat soil at the target site based on the soil-formation model.

2. The method of claim 1, wherein the remotely-sensed data includes one or both of satellite data providing imagery from remote satellite-based sensing platforms, and ranging data at least providing elevation data in remotely-sensed imagery.

3. The method of claim 1, wherein the field management information is user-supplied information that provides one or more of field boundaries, yield history, fertilization history, manure application history, and seeding rate history.

4. The method of claim 1, further comprising adjusting the customized sample design by comparing the customized sample design with one or more of expert opinion, ground truth, or historical information relative to the target site.

5. The method of claim 1, wherein the input data includes user-provided data representing similar properties in one or more additional fields comprising the target site that are proximate to the geographical location, the user-provided data representing similar properties including geo-location information identifying a location of the one or more additional field, and wherein the collection of the soil samples occurs according to the customized sample design includes selecting locations from the or more additional fields, the soil samples collected from the one or more additional fields enabling the predicting of the soil-forming environments and related properties at the target site at both of the sampled sites and the unsampled sites.

6. The method of claim 1, wherein one or more predictive models include at least one of a transferability configuration to assess soil-forming environments and related properties in sampled and unsampled fields having features that are either proximate to or not directly related to the target site from which soil samples are collected, and a semi-trained model configured to assess soil-forming environments and related properties from sampled fields having features proximate to the target site from which soil samples are collected such that a sampling density in the sampled fields is less than the sampling density in the target site from which soil samples are collected.

7. The method of claim 1, wherein the one or more digital terrain derivatives representing changes in elevation and contour in the landscape are outcomes of one or more machine learning-based landscape models that include digital hillslope position models and digital elevation models.

8. The method of claim 1, wherein the predicting one or more soil-forming environments and related properties from the collection of the soil samples further comprises applying one or more additional machine learning-based models to identify weights representing the selected parameters, model the one or more soil properties at one or both of the qualified sites and the spatially-paired helper sampling locations, and extrapolate data across the landscape.

9. The method of claim 1, wherein the target site includes one or more areas within the geographical location.

10. The method of claim 1, further comprising defining one or more management zones based on one or more soil fertility maps.

11. A system, comprising:

a data collection element configured to receive input data representing a geographical location, the input data including remotely-sensed data indicative of a landscape of the geographical location, and user input information that includes field management information relative to the geographical location;

a machine learning modeling engine configured to characterize the landscape of the geographical location to determine locations for soil sample collection following a customized sample design and model and map soil properties at a target site based on the customized sample design, by:

developing a soil-formation model for simulating seasonal soil formation and development at the target site, and organizing a plurality of soil-related data layers representing a soil-forming environment of the target site, the soil-formation model developed by:

creating a profile of terrain characteristics and land management characteristics, by identifying features that represent hillslope position, landscape features, localized features, and yield land management information for the geographical location, deriving one or more digital terrain derivatives in covariate parameters, the one or more digital terrain derivatives representing changes in elevation and contour in of the landscape across the target site, and selecting one or more soil sampling locations for a collection of soil samples based on the covariate parameters, selecting one or more variables from the covariate parameters to represent the target site in the plurality of soil-related data layers, by applying one or more regularization algorithms to reduce over-fitting in the covariate parameters, and identifying one or more qualified sample points in the customized sample design from a confluence of one or more spatial models of digital representations of the soil-forming environment in the plurality of soil-related data layers at the target site for one or more simulations by the soil-formation model, wherein the customized sample design identifies qualified sites within the target site from the one or more qualified sample points along with spatially-paired helper sampling locations identified at least from a digitized hillslope position at the target site, and predicting one or more soil properties from the collection of the soil samples for sampled and unsampled sites at the target site; and a mapping engine configured to generate one or more maps of soil fertility at the target site based on predicted soil properties of an associated soil test data within the sampled and unsampled sites, wherein the collection of the soil samples is from qualified sites identified by the one or more qualified sample points at the target site, and a user performs the collection according to the customized sample design, or an automated collection is controlled according to the customized sample design, and wherein the one or more soil properties are predicted, and the one or more models and maps of soil fertility are generated, where both soil samples have been collected and where no soil samples have been collected, and wherein agricultural equipment is automatically controlled to spatially treat soil at the target site based on the soil-formation model.

12. The system of claim 11, wherein the remotely-sensed data includes one or both of satellite data providing imagery from remote satellite-based sensing platforms, and ranging data at least providing elevation data in remotely-sensed imagery.

13. The system of claim 11, wherein the field management information is user-supplied information that provides one or more of field boundaries, yield history, fertilization history, manure application history, and seeding rate history.

14. The system of claim 11, wherein the customized sample design is adjusted by comparing the customized sample design with one or more of expert opinion, ground truth, or historical information relative to the target site.

15. The system of claim 11, wherein the input data includes user-provided data representing similar properties in one or more additional fields comprising the target site that are proximate to the geographical location, the user-provided data representing similar properties including geo-location information identifying a location of the one or more additional field, and wherein the collection of the soil samples occurs according to the customized sample design includes selecting locations from the or more additional fields, the soil samples collected from the one or more additional fields enabling the predicting of the soil-forming environments and related properties at the target site at both of the sampled sites and the unsampled sites.

16. The system of claim 11, wherein the machine learning modeling engine includes one or more predictive models that further include at least one of a transferability configuration to assess-forming environments and related soil properties in sampled and unsampled fields having features that are either proximate to or not directly related to the target site from which soil samples are collected, and a semi-trained model configured to assess-forming environments and related soil properties from sampled fields having features proximate to the target site from which soil samples are collected such that a sampling density in the sampled fields is less than the sampling density in the target site from which soil samples are collected.

17. The system of claim 11, wherein the one or more digital terrain derivatives representing changes in elevation and contour in the landscape are outcomes of one or more machine learning-based landscape models that include digital hillslope position models and digital elevation models.

18. The system of claim 11, wherein the machine learning modeling engine is further configured to apply one or more additional machine learning-based models to identify weights representing the selected parameters, model the one or more soil-forming environments and related properties at one or both of the qualified sites and the spatially-paired helper sampling locations, and extrapolate data across the landscape.

19. The system of claim 11, wherein the target site includes one or more areas within the geographical location.

20. The system of claim 11, wherein one or more management zones are defined based on the one or more maps of soil fertility.

* * * * *